(12) United States Patent
Higham et al.

(10) Patent No.: US 8,615,304 B2
(45) Date of Patent: Dec. 24, 2013

(54) DATA-DRIVEN PATTERN DETECTION OF IMPLANTABLE MEDICAL DEVICE DATA

(75) Inventors: Paul Higham, Cupertino, CA (US); Atila Amiri, Fremont, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 13/601,459

(22) Filed: Aug. 31, 2012

(65) Prior Publication Data
US 2012/0330379 A1 Dec. 27, 2012
US 2013/0211476 A9 Aug. 15, 2013

Related U.S. Application Data

(63) Continuation of application No. 12/884,021, filed on Sep. 16, 2010, now Pat. No. 8,265,753, which is a continuation of application No. 11/558,062, filed on Nov. 9, 2006, now abandoned.

(51) Int. Cl.
*A61N 1/36* (2006.01)
(52) U.S. Cl.
USPC ............. 607/59; 128/920; 128/923; 128/924; 607/1; 607/62; 607/63
(58) Field of Classification Search
None
See application file for complete search history.

(56) References Cited

U.S. PATENT DOCUMENTS

| | | |
|---|---|---|
| 6,272,377 B1 | 8/2001 | Sweeney |
| 6,400,982 B2 | 6/2002 | Sweeney |
| 6,470,210 B1 | 10/2002 | Chen |
| 2001/0020136 A1 | 9/2001 | Sweeney |
| 2002/0016550 A1 | 2/2002 | Sweeney |
| 2004/0064062 A1 | 4/2004 | Zhou |
| 2004/0116972 A1* | 6/2004 | Marcovecchio ................ 607/14 |

FOREIGN PATENT DOCUMENTS

| | | |
|---|---|---|
| EP | 1218060 | 7/2002 |
| WO | 0124876 | 4/2001 |
| WO | 2004028632 | 4/2004 |

OTHER PUBLICATIONS

Non-Final Office Action mailed Dec. 18, 2009: Related U.S. Appl. No. 11/558,062.
Final Office Action mailed Jun. 16, 2010: Related U.S. Appl. No. 11/558,062.
Advisory Action mailed Sep. 7, 2010: Related U.S. Appl. No. 11/558,062.
Non-Final Office Action mailed Dec. 7, 2011: Related U.S. Appl. No. 12/384,021.
Notice of Allowance mailed May 10, 2012: Related U.S. Appl. No. 12/884,021.

* cited by examiner

*Primary Examiner* — Deborah Malamud
(74) *Attorney, Agent, or Firm* — Theresa Raymer; Steven M. Mitchell

(57) ABSTRACT

Detecting patterns in sensed implantable medical device (IMD) data is described. One implementation involves an IMD that includes a data-driven pattern detection network embodied on the IMD to detect a pattern from sensed patient data. The IMD also includes one or more algorithms embodied on the IMD to utilize the pattern to effect patient therapy.

20 Claims, 7 Drawing Sheets

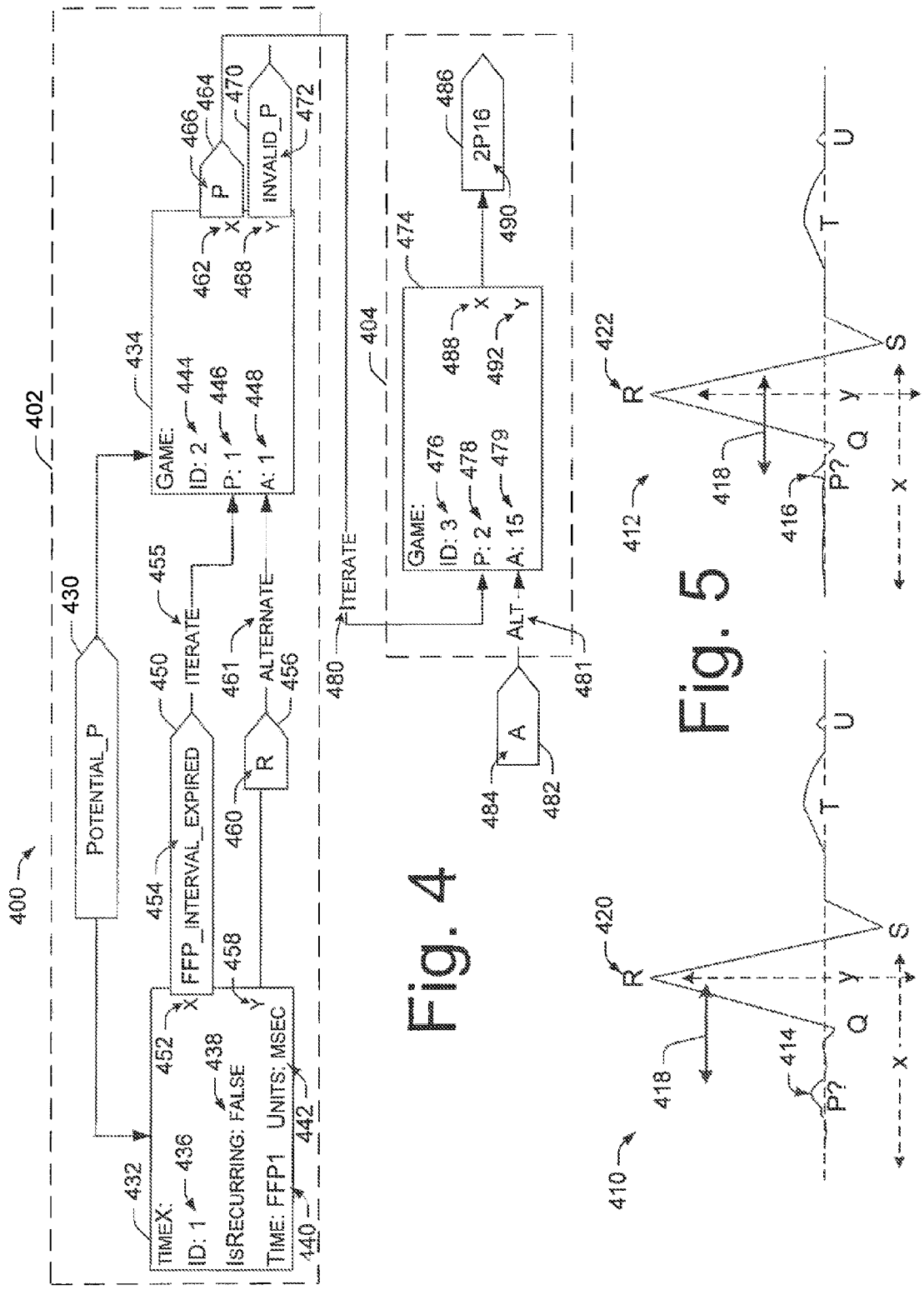

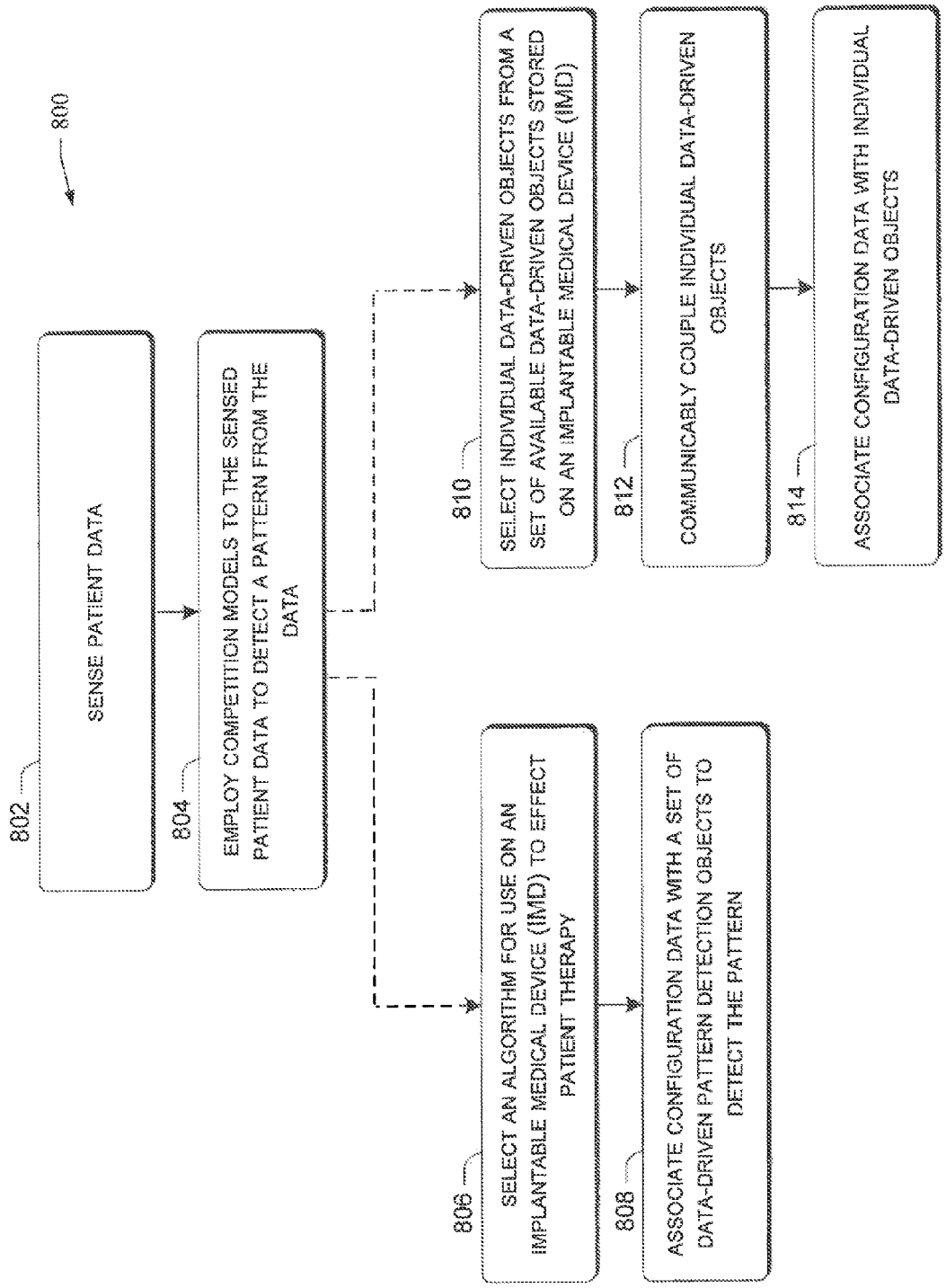

DATA-DRIVEN PATTERN DETECTION OF IMPLANTABLE MEDICAL DEVICE DATA

PRIORITY CLAIM

This application is a Continuation application of and claims priority and other benefits from U.S. patent application Ser. No. 12/884,021, filed Sep. 10, 2010, now U.S. Pat. No. 8,265,753, entitled "DATA-DRIVEN PATTERN DETECTION OF IMPLANTABLE MEDICAL DEVICE DATA", which is a continuation of U.S. patent application Ser. No. 11/558,062, filed Nov. 9, 2006, now abandoned. U.S. Pat. No. 8,265,753 is incorporated herein by reference in its entirety.

TECHNICAL FIELD

The present invention generally relates to implantable medical devices for sensing patient data and/or delivering patient therapies.

BACKGROUND

Implantable medical devices (IMDs) are utilized to monitor and/or treat assorted patient conditions. Some of the most commonly employed IMD's relate to cardiac function. Implantable cardiac devices (ICDs), such as pacemakers and defibrillators, sense or monitor many different parameters that may be used to determine a patient's cardiac health and/or overall patient health. For instance, implantable cardiac devices can sense morphology-related parameters, impedance, intrinsic heart rate, heart rate recovery, heart rate variability, conduction delay, pressure, posture, activity, blood chemistry, and so forth. Sensed data can be processed by specific code of the IMD to detect a pattern of the data. Presently, detection of a different pattern requires significant rewriting of the IMDs code and subsequent testing. Among other concerns, new technologies for improving patient health are slowed by IMD configurations that require rewriting of code to detect different patterns.

SUMMARY

Detecting patterns in sensed implantable medical device (IMD) data is described. One implementation involves an IMD that includes a data-driven pattern detection network embodied on the IMD to detect a pattern from sensed patient data. The IMD also includes one or more algorithms embodied on the IMD to utilize the pattern to effect patient therapy.

Another implementation includes a technique which senses patient data with an IMD. The technique also employs competition models on the IMD to detect a pattern from the sensed patient data.

BRIEF DESCRIPTION OF THE DRAWINGS

FIG. 4 illustrates an example of a data-driven pattern detection network in accordance with one implementation.

FIG. 5 illustrates a representation of two electrocardiograms for purposes of explanation in relation to sensed patient data.

FIG. 8 illustrates a flow diagram of a process for accomplishing pattern detection of IMD data in accordance with one implementation.

DETAILED DESCRIPTION

Overview

Figure 1:
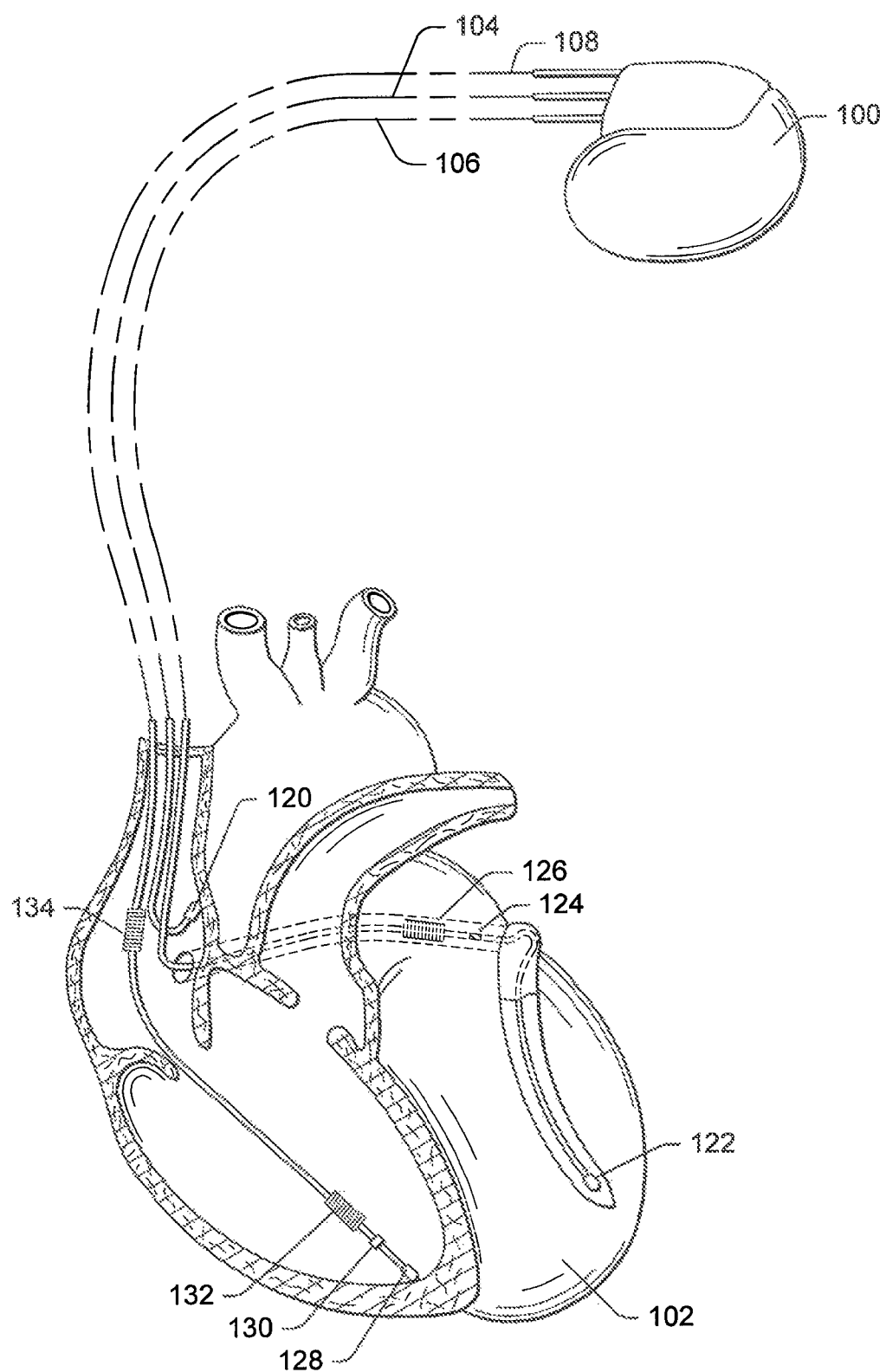
FIG. 1 illustrates a diagrammatic representation of an implantable medical device in electrical communication with a patient's heart for multi-chamber sensing and delivery of multi-chamber stimulation and shock therapy in accordance with one implementation.

The following discussion relates to implantable medical devices (IDMs) configured to accomplish pattern detection of patient data. The pattern detection can be accomplished by employing competition models which score competing events to detect an emerging pattern (or lack thereof). Competition models can be accomplished on data-driven objects which are customized to detect a specific pattern via configuration data. Changing the configuration data allows the same data-driven object to detect a different pattern. In some instances data-driven objects are communicably coupled into a data-driven pattern detection framework for detecting patterns which may not be readily detected with a single data-driven object.

The detected patterns can be utilized by algorithms employed on the IMD. For instance, in a cardiac context assume that a particular algorithm performs a function x when a pattern y is detected. Pattern y, for example, can be an occurrence of two P-waves in 16 cardiac cycles (2P16). The data-driven pattern detection framework detects for the algorithm whether pattern y occurred. The algorithm can implement function x upon detection of pattern y. In such a case if the 2P16 pattern is detected, the algorithm may decrease a pacing rate and rely more upon intrinsic pacing.

The data-driven objects are data-driven in that changing the configuration data is sufficient to cause an object and/or objects to detect a different pattern. For instance, simply by changing the configuration data from 2P16 to 2P17 causes the data-driven objects to detect a different pattern (e.g., 2 P-waves in 17 cardiac cycles rather than 2 P-waves in 16 cardiac cycles). The configuration data can be changed to reflect a desired pattern without changes to the objects themselves or their relative inter-relationships (e.g., data-driven pattern detection framework). Accordingly, the data-driven pattern detection framework allows changes to an IMD's algorithms and/or addition of new algorithms with reduced or no rewrite of the IMD's code. In such an instance, the data-driven pattern detection framework performs pattern detection for the new or altered algorithm by changing configuration data associated with the detection framework and/or by recombining known data-driven objects to detect the desired pattern. A relatively small number of different data-driven objects can be inter-related in various network configurations to detect a wide range of patterns. For instance, a relatively small number of different objects can be organized in different networks and with different configuration data to detect a multitude of different patterns.

Several examples of data-driven pattern detection in IMDs are described below in a cardiac context as implantable cardiac devices. Implantable cardiac devices are commonly characterized as a miniature computing device that is implanted into the body of a patient to monitor, regulate, and/or correct heart activity. Such devices include implantable cardiac stimulation devices (e.g., implantable cardiac pacemakers, implantable defibrillators, cardiac rhythm management devices) that apply stimulation therapy to the heart and implantable cardiac monitors that monitor and record heart activity for diagnostic purposes.

Implantable Cardiac System

FIG. 1 shows an exemplary implantable medical device (IMD or "device") 100 in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage. The right atrial lead 104 enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
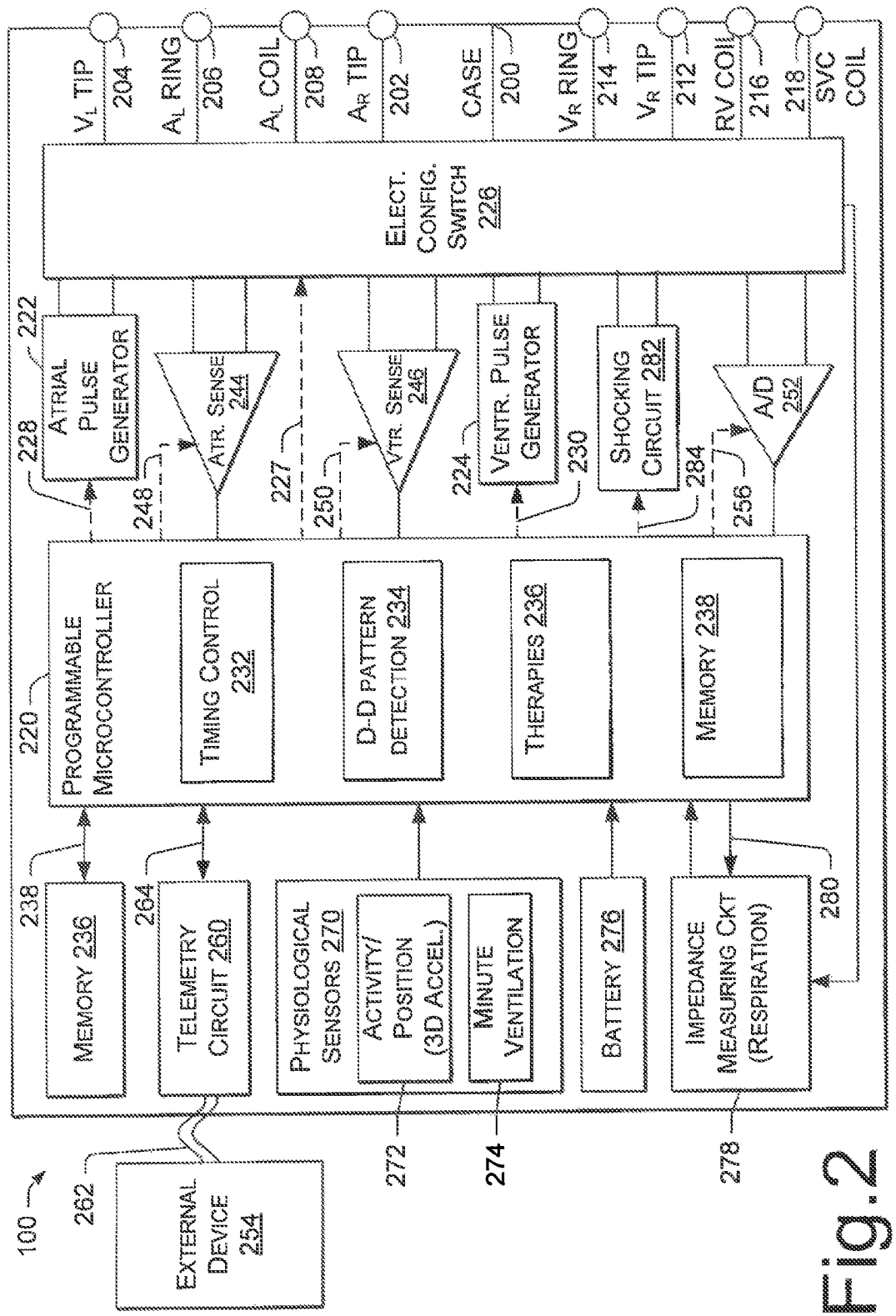
FIG. 2 illustrates a functional block diagram of the multi-chamber implantable medical device in accordance with one implementation.

FIG. 2 shows an exemplary, simplified block diagram depicting various components of the implantable cardiac device 100. The components are housed in housing 200, which is often referred to as the "can", "case", "encasing", or "case electrode". Housing 200 may be programmably selected as a return electrode for unipolar modes or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals), including:

a right atrial tip terminal (AR TIP) 202 for atrial tip electrode 120;
a left ventricular tip terminal (VL TIP) 204 for left ventricular tip electrode 122;
a left atrial ring terminal (AL RING) 206 for left atrial ring electrode 124;
a left atrial shocking terminal (AL COIL) 208 for left atrial coil electrode 126;
a right ventricular tip terminal (VR TIP) 212 for right ventricular tip electrode 128;
a right ventricular ring terminal (VR RING) 214 for right ventricular ring electrode 130;
a right ventricular shocking terminal (RV COIL) 216 for RV coil electrode 132; and
an SVC shocking terminal (SVC COIL) 218 for SVC coil electrode 134.

The implantable medical device 100 includes a programmable microcontroller 220 that controls various operations, including cardiac monitoring and stimulation therapy. Microcontroller 220 includes a microprocessor (or equivalent control circuitry), RAM and/or ROM memory, logic and timing circuitry, state machine circuitry, and I/O circuitry.

Device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, combipolar, etc.) by selectively closing the appropriate combination of switches. To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atria-ventricular (AV) delay, atrial interconduction (A-A) delay, or ventricular interconduction (V-V) delay, etc.). The timing control circuitry may also be used for the timing of refractory periods, blanking intervals, noise detection windows, evoked response windows, alert intervals, marker channel timing, and so on.

Microcontroller 220 is also equipped with a data-driven pattern detection component 234, a therapies component 236 and a memory component 238. The data-driven pattern detection component 234 employs competition models to analyze parameter data sensed or otherwise obtained by IMD 100 to detect patterns in the data. In this configuration, the data-driven pattern detection component includes an object based network or framework and associated configuration data executable by the microcontroller to provide pattern detection functionalities to various algorithms of the IMD such as algorithms employed on the therapies component 236 and/or the timing control circuitry 232. Accordingly, the algorithms can effect patient therapy responsive to the detected patterns.

The components 232, 234, 236, and 238 may be implemented in hardware as part of the microcontroller 220, or as software/firmware instructions programmed into the device and executed on the microcontroller 220 during certain modes of operation. These components may further be implemented independent from the microcontroller 220. Although not shown, the microcontroller 220 may further include other dedicated circuitry and/or firmware/software components that assist in monitoring various conditions of the patient's heart and managing pacing therapies.

The implantable medical device 100 has atrial sensing circuits 244 and ventricular sensing circuits 246 to detect the presence of cardiac activity in each of the four chambers of the heart. The sensing circuits 244 and 246 may be selectively coupled to the right atrial lead 104, coronary sinus lead 106, and the right ventricular lead 108 through the switch 226. The sensing circuits 244 and 246 may include dedicated sense amplifiers, multiplexed amplifiers, or shared amplifiers. Switch 226 determines the "sensing polarity" of the cardiac signal by selectively dosing the appropriate switches. In this way, the clinician may program the sensing polarity independent of the stimulation polarity. Each sensing circuit 244 and 246 may employ one or more low power, precision amplifiers with programmable gain and/or automatic gain control, band pass filtering, and threshold detection circuitry to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

The implantable medical device 100 is further equipped with an analog-to-digital (A/D) data acquisition system 252 to sample cardiac signals across any pair of desired electrodes. The system 252 is coupled to the right atrial lead 104, the coronary sinus lead 106, and the right ventricular lead 108 through the switch 226. Cardiac signals received from the leads are supplied to the data acquisition system 252, which is configured to acquire intracardiac electrogram (IEGM) signals, convert the raw analog data into a digital signal, and store the digital signals for processing.

The data acquisition system 252 is coupled to the microcontroller 220, or other detection circuitry, to assist in detecting various parameters and events. For instance, the system 252 acquires the data utilized by the data-driven pattern detection component 234 to detect patterns in the data. The data acquisition system 252 is further configured to detect an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The data acquired by the data acquisition system 252 is stored in memory 238 and can be subsequently transmitted to an external device 254. The external device 254 may be implemented hi many ways, including as a programmer, a transtelephonic transceiver, or a diagnostic system analyzer. Additionally, the external device 254 may be representative of an intermediate communication device that receives information from the implantable device and relays the information to another device or system for evaluation. In this manner, sensed data and/or associated patterns detected by the data-driven pattern detection component 234 can be output to the external device 254 for further analysis or presentation to the clinician.

In one implementation, a telemetry circuit 260 facilitates communication between the implantable device 100 and the external device 254. During programming or data output, the telemetry circuit 260 establishes a communication link 262 with the external device 254. In addition to downloading data to the external device, operating parameters for the implantable device 100 may be non-invasively programmed into the memory 238 by transmission from the external device 254 over link 262 and through the telemetry circuit 260. The microcontroller 220 activates the telemetry circuit 260 with a control signal 264. The telemetry circuit 260 allows intracardiac electrograms and status information relating to the operation of the device 100 (as contained in the microcontroller 220 or memory 238) to be sent to the external device 254 through an established communication link 262.

The implantable device 100 may include magnet detection circuitry (not shown), coupled to the microcontroller 220, to detect when a magnet is placed over the device 100. A magnet may be used by a clinician to perform various test functions of the device 100 and/or to signal the microcontroller 220 that the external device 254 in the form of a programmer is in place to receive or transmit data to the microcontroller 220 through the telemetry circuit 260.

The implantable medical device 100 can further include one or more physiologic sensors 270. Such sensors are commonly referred to as "rate-responsive" sensors because they are typically used to adjust pacing stimulation rates according to the exercise state of the patient. However, the physiological sensor(s) 270 may further be used to detect changes in cardiac output, changes in the physiological condition of the heart, diurnal changes in activity (e.g., detecting sleep and wake states), or respiration activity (e.g., minute ventilation). The microcontroller 220 responds to changes sensed by the sensor (s) 270 by adjusting various pacing parameters (such as rate, AV Delay, V-V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient. Examples of physiologic sensors that may be implemented in device 100 include sensors that, for example, sense respiration activities, $O_2$ saturation, evoked response, pH of blood, and so forth.

In the illustrated implementation, the physiological sensors 270 include sensors for detecting patient activity and respiration. Any sensor capable of sensing such conditions, either directly or indirectly, may be used. In particular, the physiological sensors 270 include an activity sensor 272 to detect patient movement. The activity sensor 272 may be implemented in many ways, including as a three-dimensional (3D) DC accelerometer. In one configuration, the accelerometer output signal is bandpass-filtered, rectified, and integrated at regular timed intervals. The processed accelerometer signal is used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting state. The activity variance can be monitored diurnally to detect the low variance in the measurement corresponding to the sleep state.

An exemplary physiological sensor used to detect respiratory conditions is a minute ventilation (MV) sensor 274. The MV sensor 274 senses minute ventilation, which is the total volume of air that moves into and out of a patient's lungs in a minute. The MV sensor 274 uses transthoracic impedance, which is a measure of impedance across the chest cavity, to sense air movement. Lungs filled with air have higher impedance than empty lungs. Thus, upon inhalation, impedance increases and upon exhalation, impedance decreases. Other respiration sensors that may be used in addition to, or instead of, the MV sensor 274 include an $O_2$ sensor that measures oxygen-related parameters, a sensor to measure respiration rate, and a sensor to measure tidal volume.

The implantable medical device 100 additionally includes a battery 276 to supply operating power to various components shown in FIG. 2. The battery 276 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 276 also has a predictable discharge characteristic so that elective replacement time can be detected. As one example, the device 100 employs lithium/silver vanadium oxide batteries.

The implantable medical device 100 further includes an impedance measuring circuit 278 that is enabled by the microcontroller 220 via a control signal 280. The impedance measuring circuit 278 is used for many things, including: lead impedance surveillance during the acute and chronic phases for proper lead positioning or dislodgement, detecting operable electrodes and automatically switching to an operable pair if dislodgement occurs; measuring thoracic impedance for many uses including determining shock thresholds; detecting when the device has been implanted; measuring stroke volume; and detecting the opening of heart valves; and so forth. The impedance measuring circuit 278 can be used to measure respiration-related parameters, such as respiration rate, minute ventilation, respiration signal amplitude, and tidal volume. The impedance measuring circuit 278 is coupled to the switch 226 so that any desired electrodes may be used.

The device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 Joules), moderate (e.g., 0.5-10 Joules), or high energy (e.g., 11 to 40 Joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV coil electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Data-Driven Pattern Detection Network Models

Figure 3:
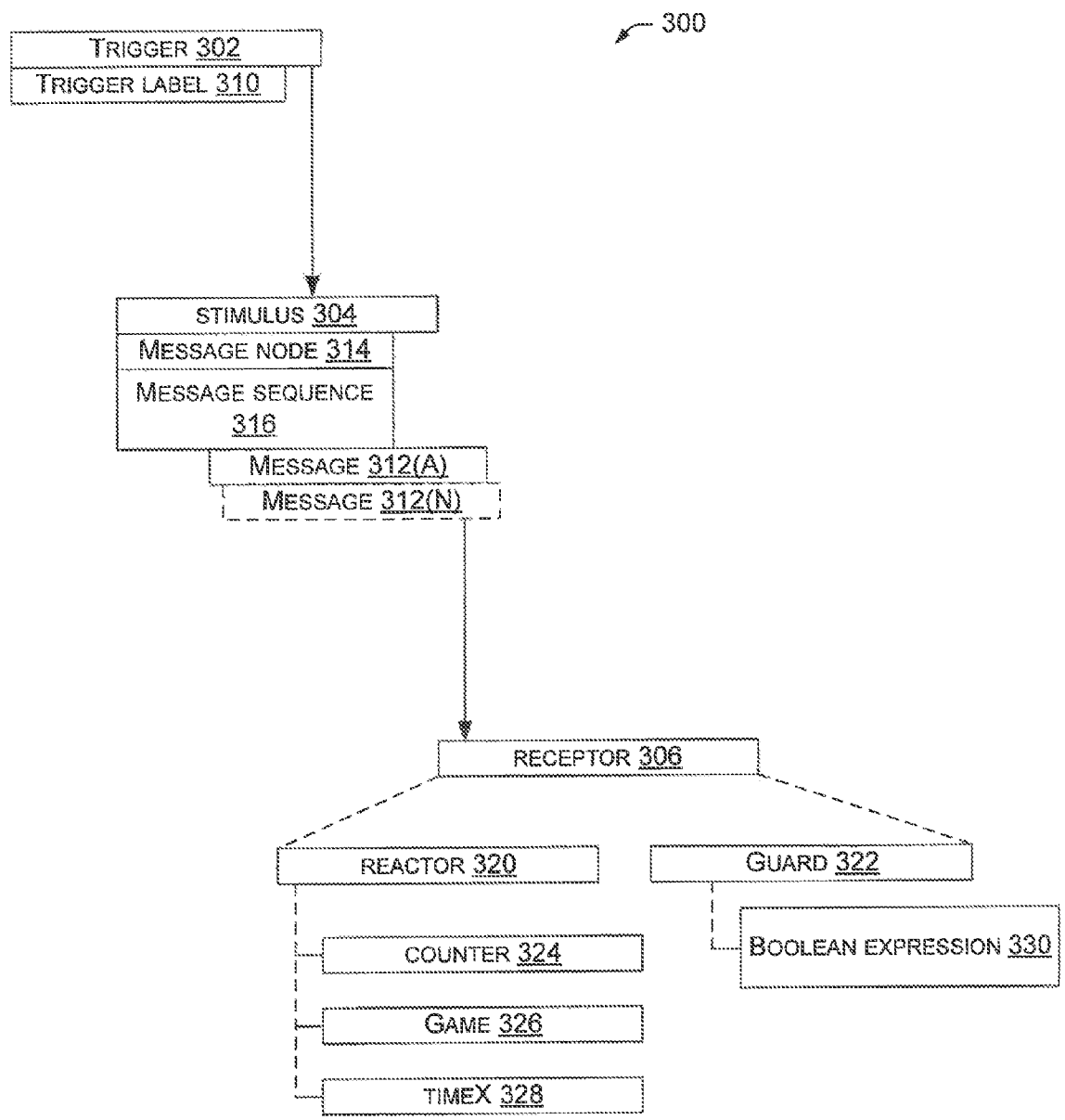
FIG. 3 illustrates a model of exemplary components of a data-driven pattern detection network in accordance with one implementation.

FIG. 3 illustrates a data-driven pattern detection network model 300 and associated exemplary data-driven pattern detection objects (hereinafter "data-driven objects"). Data-driven pattern detection network model 300 offers a platform for employing competition models to detect patterns in patient data.

Figure 6:
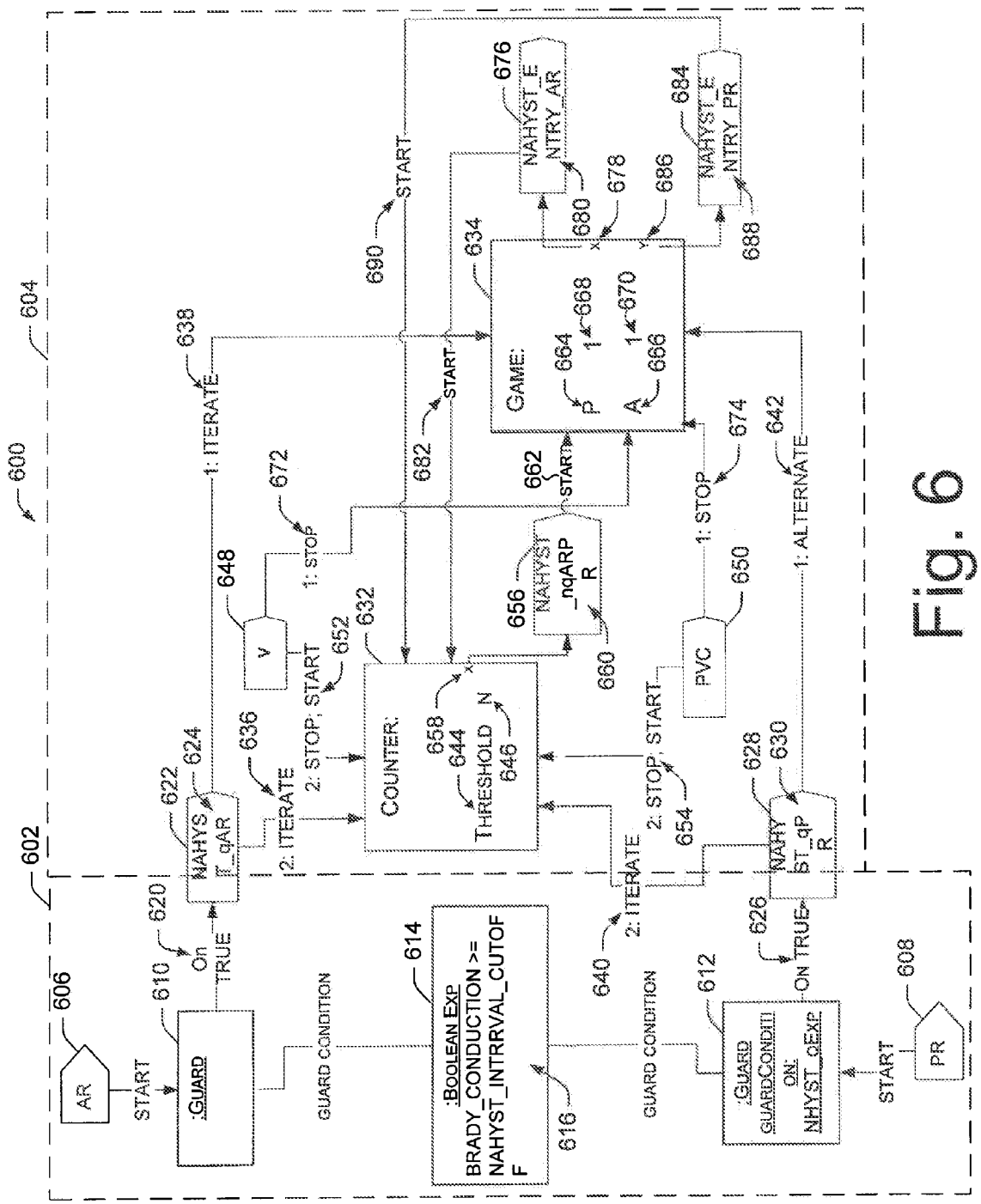
FIGS. 6-7 illustrate further examples of data-driven pattern detection networks in accordance with one implementation.
Figure 7:
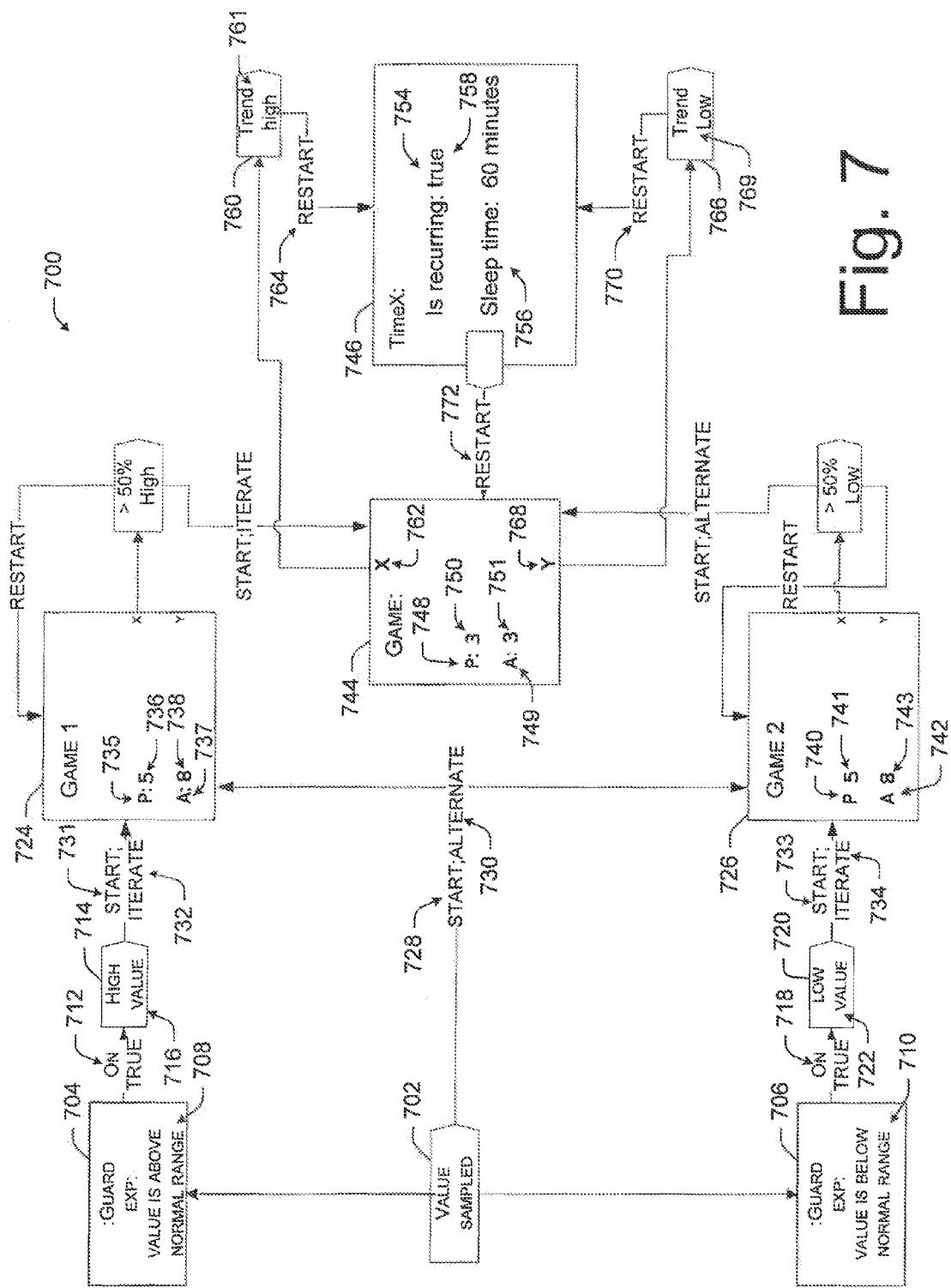

The data-driven objects of model 300 are introduced in a generic manner in relation to FIG. 3 and are further explained by way of example in relation to FIGS. 4, and 6-7. Further, data-driven pattern detection network model 300 can be employed by the data-driven pattern detection component 234 described above in relation to FIG. 2. The data-driven pattern detection network objects described below can be utilized to detect any number of different patterns from patient data as should become apparent from the description below.

In this instance data-driven pattern detection network objects of model 300 include a trigger 302, a stimulus 304, and a receptor 306. A trigger is a representation of a pattern or an event. A trigger label 310 of the trigger 302 denotes the pattern of the trigger. Firing of the trigger 302 causes delivery of the stimulus 304 to the receptor 306 which is connected to the trigger. Stated another way, stimulus 304 is a medium used by trigger 302 to induce reaction in the receptor 306.

Delivering stimulus 304 to receptor 306 sends message(s) 312(A)-312(N) specified in a message node 314. Within a message node 314, a message Sequence 316 orders the messages 312(A)-312(N) for relative delivery to the receptor 306.

Data-driven pattern detection network model 300 includes two basic types of receptors known as reactors 320 and guards 322. Reactors 320 are receptors which are driven by triggers and can fire either one or two other triggers. Reactors can be started and stopped, and can be iterated and alternated as will be explained below. Reactors fire triggers after some delay (e.g. when some accumulated score reaches a set threshold). Data-driven pattern detection network model 300 includes three basic types of reactors 320 in the form of counter 324, game 326, and timeX 328.

Counter 324 is a simple reactor type that is used for counting occurrence of events and patterns. Game 326 is a reactor that models a competition between two opponents. For instance, if the opponents are called opponents X (or protagonist) and Y (or antagonist), X scores a point whenever the game receives an iterate message and Y scores a point whenever the game receives an alternate message.

TimeX 328 serves to compare one or more conditions against a time duration (e.g. does a condition occur within a pre-defined time duration).

Guard 322 is a receptor used to qualify other patterns based on some condition known as the guard condition. The guard condition is expressed as a Boolean expression 330 referenced by the guard. The primacy use of guard 322 is to constrain delivery of stimuli 304 to receptors 306. The above mentioned data-driven objects are but examples and other data-driven objects can be employed which are consistent with the description above and below.

FIG. 4 illustrates an example of a data-driven pattern detection network 400 which utilizes the basic pattern detection objects described above in relation to FIG. 3 to detect a pattern from patient data obtained by an IMD. In this instance, assume that the IMD is employed in a cardiac setting for purposes of explanation. This particular data-driven pattern detection network 400 includes two distinct sub-units 402, 404 each of which functions as a separate data-driven pattern detection network. Sub-unit 402 functions to determine whether a sensed pulse is a P-wave of a cardiac cycle or not. P-waves are described below in relation to FIG. 5, Sub-unit 404 functions to determine whether 2 P-waves occur in 16 cardiac cycles. In this particular configuration, the output of sub-unit 402 functions as a stimulus for sub-unit 404. Stated another way, sub-unit 402 cascades into sub-unit 404.

Before continuing with the discussion of FIG. 4 consider hypothetical cardiac cycles 410, 412, such as could be obtained from an electrocardiogram (ECG), illustrated in FIG. 5. Various cardiac diagnostic algorithms utilize an occurrence of P-waves to determine a cardiac condition. A P-wave represents an intrinsic cardiac event specifically relating to atrial depolarization. A P-wave can be detected and registered on an electrocardiogram. However, other cardiac events and/or noise may be detected which can be mistaken for a P-wave. One technique for determining whether a sensed P-wave is an actual P-wave or some other signal such as a signal generated in the ventricle is to compare a time duration between the detected event and an occurrence of an R-wave in the QRS complex. This duration is sometimes referred to as the far field protection (FFP) duration.

For purposes of explanation consider cardiac cycle 410 which illustrates a sensed potential P-wave (P?) 414 (which in this instance is a real P-wave) and consider cardiac cycle 412 which illustrates another sensed potential P-wave (P?) 416 (which in this instance is actually a ventricular event). In cardiac cycle 410, the FFP duration is indicated as arrow 418 which begins at P?-wave 414 and extends toward R-wave 420. In the instance of cardiac cycle 410, the FFP duration 418 concludes before the occurrence of the R-wave 420 occurs as compared along the vertical or y-axis (where the horizontal or x-axis represents time). Contrastingly, in cardiac cycle 412, the R-wave 422 occurs during the FFP duration 418 when compared along the vertical or y-axis.

Returning to FIG. 4, data-driven pattern detection network 400 leverages the FFP duration to determine if a sensed potential P-wave is an actual P-wave or a non-P-wave. Specifically, sub-unit 402 receives a trigger event as a potential P-wave at 430. Upon receiving the potential P-wave sub-unit 402 starts timeX 432 and game 434. TimeX 432 includes an ID field set at "1" as indicated at 436 which indicates that the timeX is the first reactor of data-driven pattern detection network 400. At 438, the timeX indicates that it is not detecting a recurring pattern since each potential P-wave is considered independently in sub-set 402. Finally, the timeX indicates that the test duration is determined by a pre-established FFP interval as indicated at 440 and that the duration is measured in milliseconds as indicated at 442. Game 434 has an ID "2" as indicated at 444 and which delineates game 434 as the second reactor of data-driven pattern detection network 400. Game 434 has a protagonist and an antagonist, each having a value set to a threshold of 1 as indicated at 446, 448 respectively. Once the timeX 432 and game 434 are started, one of two possibilities can occur. One possibility is the FFP interval expires first resulting in a trigger 450 being fired by the timeX's x port 452.

In this case, trigger 450 relates to an "FFP_interval-expired" message 454 which is sent along with an iterate command 455 to protagonist 446. Alternatively, an R wave occurs resulting in a trigger 456 being fired from the timeX's y-port 458 and delivering an R-wave message 460 to antagonist 448 along with an alternate command 461.

Since both the protagonist and antagonist values 446, 448 of game 434 are set to a threshold of 1, receiving either an iterate command 455 or an alternate command 461 meets the threshold and causes game 434 to fire its own trigger. If an iterate command 455 is received by game 434 due to the FFP interval expiring then protagonist 446 causes x-port 462 to fire a trigger 464. Trigger 464 conveys a P-wave message 466. P-wave message 466 indicates that a P-wave was detected. If the alternate trigger 456 is received by game 434 then antagonist 448 causes y-port 468 to send a trigger 470 which conveys an invalid P-wave message 472. (In this particular configuration, the invalid P-wave trigger is not utilized in further processing and hence is not connected to any components.)

Sub-set 404 includes a game 474, which is identified as the third '3' reactor as indicated at 476 of data-driven pattern detection network 400. Game 474 functions to determine an incidence of intrinsic atrial depolarization (e.g., P-wave) in relation to paced atrial depolarization or A-wave. So for instance, in a given number of cardiac cycles, for example 16, did intrinsic atrial depolarization occur a pre-established number of times, say for example 2, or not. An algorithm can utilize this information in effecting patient therapy.

Game 474 has a protagonist that has a threshold set at '2' as indicated at 478 and an antagonist that has a threshold set at 15 as indicated at 479. Protagonist 478 receives an iterate stimulus 480 from trigger 464. Antagonist 479 receives an alternate stimulus 481 from a trigger 482 along with a message 484 that an A-wave occurred.

Assume for purposes of explanation that game 474 is started at the time a potential P-wave is received as indicated at 430, and that protagonist 478 and antagonist 479 have scores of zero. Further assume that the first event is that a P-wave is detected by subset 402 and trigger 464 fires and delivers iterate command 480 to protagonist 478. The iterate command causes the protagonist to increase its score by a value of one and to compare its updated score to its threshold. In this instance the protagonist's score is now 1 and its threshold as mentioned above is 2. Since the score is less than the threshold, the game continues to receive further stimulus. Assume further that the next event is detection of an A-wave. Alternate command 481 is delivered to antagonist 479 via trigger 482. The alternate command causes the antagonist to increase its score by a value of one and compare the score to its threshold. As mentioned above, the antagonist 479 in this example has a threshold of 15. Since the score (e.g., 1) is less than the threshold, game 474 continues to receive stimulus. Now assume that the next event is another iterate command 480 delivered to protagonist 478. The protagonist increases its score by a value of one and compares the score to its threshold as indicated at 478. In this instance, the score is now two which equals its threshold, The protagonist issues a stop command and fires its own trigger 486 from x-port 488 which contains a message 490 that the 2P16 condition has occurred. This trigger 486 can then be utilized by various algorithms (not shown) to effect patient therapy. At this point game 474 awaits a start command to begin the process again.

In an alternative scenario assume that after receiving the first iterate command 480 that game 474 receives 15 straight alternate commands 481 for the antagonist 479. In such a scenario, the antagonist's score equals its threshold of 15, the antagonist issues a stop command. In this scenario, 16 events are received (one P-wave and 15 A-waves) without 2 P-waves occurring. As such the 2P16 condition was not detected. In this particular configuration, no stimulus is produced when the 2P16 condition fads (e.g. the antagonist wins), but the skilled artisan should recognize that such a stimulus can be triggered from y-port 492. At this point game 474 awaits a subsequent start command. A stop command followed by a start command functions to reset the game with all scores at zero.

An attribute of data-driven pattern detection network 400 is that individual reactors can be readily adapted to provide pattern detection for new or different algorithms. For instance, assume that a new algorithm is developed which utilizes a "3P20" configuration. In such an instance, the protagonist threshold value at 478 of game 474 is simply adjusted from 2 to 3 and the antagonist threshold value at 479 is adjusted from 15 to 19. Other changes or re-writes are reduced and/or eliminated.

FIG. 6 illustrates an example of another data-driven pattern detection network 600 which utilizes the pattern detection objects described above in relation to FIG. 3 to detect another different pattern. This pattern detection network is configured to detect patterns which can be utilized, for instance, by a negative entry hysteresis algorithm, among others to effect patient therapy. For example, when specific patterns are detected by the pattern detection network, a negative entry hysteresis algorithm may increase an IMD pacing rate beyond a base pacing rate to limit intrinsic cardiac pacing.

For purposes of explanation, data-driven pattern detection network 600 is divided into two sub-units 602, 604. Sub-unit 602 detects two different pairs of events or triggers. The first pair as indicated at 606 is an AR event which is a paced atrial A-wave followed by an intrinsic ventricular R-wave. The second pair of events as indicated at 608 is a PR event which is an intrinsic atrial P-wave followed by an intrinsic ventricular R-wave. For purposes of explanation, an interval between the first and last event of a given pair can be considered a Bradycardia (Brady) conduction interval. For instance, in relation to a given pair of events a Brady conduction interval between an A-wave (or P-wave) and the corresponding R-wave may be, for example, 200 milliseconds (ms). In another instance, the Brady conduction interval might be 125 ms or 225 ms. These example values are provided for discussion purposes and are not intended to be limiting in any manner.

Sub-unit 602 includes three basic components including two guards 610, 612 and a Boolean condition 614. The guards 610, 612 function to block event pairs (e.g., AR or PR) which do not satisfy the Boolean condition 614 and to fire triggers for those pairs which do satisfy the Boolean condition. In this instance, the Boolean condition 614 relates to whether the Brady conduction interval is greater than or equal to a pre-established duration expressed as the negative A hysteresis interval cutoff. The Boolean condition 614 is expressed specifically at 616 as Brady Conduction>=NAHYST Interval Cutoff. For purposes of the ongoing discussion of FIG. 6 assume that the NAHYST Interval Cutoff is set at 150 ms, though of course other values could be utilized.

By way of example, consider that an AR trigger event 606 having an A-wave to R-wave Brady conduction interval of 200 ms is received at guard 610. In such an instance, the AR trigger event 606 satisfies the guard condition since the 200 ms AR interval is greater than the NAHYST Interval Cutoff of 150 ms. In such a scenario, the guard condition is satisfied or true. As indicated at 620 a true condition causes the guard to fire trigger 622. The trigger 622 conveys a message "NAHYST_qAR" 624 which indicates that an AR event was received that satisfied the negative hysteresis interval cutoff condition.

Similarly, consider that a PR trigger event 608 having a P-wave to R-wave Brady interval of 225 ms is received at guard 612. In such an instance, the PR event 608 satisfies the guard condition since the 225 ms PR interval is greater than the NAHYST Interval Cutoff of 150 ms. Accordingly, in this scenario, the guard condition is satisfied or true. As indicated at 626 a true condition causes the guard to fire trigger 626 conveying a message "NAHYST_qPR" 630 which indicates that a PR trigger event was received which satisfied the negative hysteresis interval cutoff condition. Conversely, consider that a PR event 608 having a P-wave to R-wave interval of 125 ms is received at guard 612. In such an instance, the PR trigger event 608 does not satisfy the guard condition since the 125 ms PR interval is not greater than (e.g., is less than) the NAHYST interval Cutoff of 150 ms. In such a scenario, the guard condition is false and guard 612 does not fire trigger 628.

To summarize, sub-set 602 individually receives AR and PR trigger events and checks the individual events against a pre-established guard condition. When an individual AR trigger event satisfies the guard condition a trigger 622 is fired indicating the occurrence of an AR trigger event satisfying the guard condition as message 624. Similarly, when an individual PR trigger event satisfies the guard condition, a trigger 628 is fired indicating the occurrence of a PR event satisfying the guard condition as message 630.

Sub-set 604 includes two reactors: a counter 632 and a game 634. Counter 632 functions to detect whether a threshold number of consecutive AR and/or PR events occur. Game 634 functions only after counter 632 has counted its threshold number of AR and/or PR sequences and has stopped. The purpose of game 634 is to identify if the event following the preceding AR/PR sequences that were counted by the counter is an AR event or a PR event.

Both the counter 632 and the game 634 are coupled to triggers 622, 628. Trigger 622 provides an iterate command function at both counter 632 and game 634 as is evidenced at 636, 638 respectively. Note, that in this implementation a relative order in which the stimuli are delivered can be pre-defined. For instance, the '1' designation of iterate command 638 and the '2' designation of iterate command 636 denote that iterate command 638 is sent first, followed by iterate command 636. The relative order of delivery can affect the functionality of the data-driven pattern detection network 600. Similar to trigger 622, trigger 628 provides an iterate command function to counter 632 as indicated at 640 and an alternate command function 642 to game 634. As indicated in the Figure the relative order of delivery for trigger 628 is the alternate command 642 then the iterate command 640.

Counter 632 has a threshold 644 set to a value n at 646. As mentioned above the triggers 622, 628 deliver an iterate command to counter 632. So whenever, the counter receives AR trigger 622 or PR trigger 628, the counter increases it score by one and compares the score to the threshold value n as indicated at 646.

Sub-set 604 also is configured to receive a V-wave event 648 and a PVC event 650. A V-wave is the signal which stimulates ventricular contraction. A PVC or premature ventricular contraction is a sensed ventricular event which is not preceded by a paced or intrinsic atrial event. As indicated at 652 and 654 respectively, the V-wave event 648 and the PVC event 650 issue stop then start commands (e.g., reset) to counter 632. The stop command makes the counter unreceptive to further stimulus. The start command causes the counter to reset its scores to zero and to again be receptive to stimulus. In summary, counter 632 is restarted upon detection of V-wave trigger event 648 or a PVC trigger event 650. Once started, counter 632 serves to detect whether a consecutive sequence of AR and/or PR events, satisfying Boolean condition 614, equals a threshold value without interruption by another V-wave or PVC. In such an instance, the counter fires trigger 656 from its x-port 658. In contrast, if another V-wave or PVC is detected before the counter's score equals the threshold value 646 then the counter resets itself to a score of zero and begins again.

Game 634 functions to identify if an event following the preceding AR/PR sequences that were counted by the counter is an AR event or a PR event (e.g., is the event directly following the one that caused counter 632 to meet its threshold an AR event or a PR event). Trigger 656 conveys a message "NAHYST nqARPR" 660 which specifies that a predetermined number of AR and/or PR events occurred without interruption by a V-wave or a PVC. Trigger 656 issues a start command 662 to game 634. Game 634 has a protagonist 664 and an antagonist 666, each having a threshold value of 1 as indicated at 668, 670 respectively. As mentioned above, trigger 622 issues an iterate command 638 to game 634 such that protagonist 664 increases its score by one and compares the updated score to its threshold 668. Similarly, trigger 628 conveying message 630 issues an alternate command 642 such that antagonist 666 increases its score by one and compares the updated score to its threshold 670. An occurrence of V-wave 648 issues a stop command 672 to game 634. Similarly, an occurrence of PVC 650 issues a stop command 674 to game 634. Note that an occurrence of V-wave 648 produces two stimulus commands: first stop command 672 indicated as '1: stop' and then the iterate command 636 indicated as '2: stop; start'. Similarly, an occurrence of PVC 650 first produces stop command 674 and then the stop; start command 654.

Assume for purposes of example, that game 634 is stopped with protagonist and antagonist (664, 666) having scores of zero. Assume further that trigger 656 issues start command 662 upon counter 632 receiving a threshold number of uninterrupted AR and/or PR events. Start command 662 causes game 634 to be receptive to iterate and alternate commands 638, 642 and stop commands 672, 674.

So for purposes of explanation, assume that the event following the one that caused counter 632 to reach its threshold and to ultimately issue start command 662 is an AR event embodied as trigger 622. The trigger 622 also delivers iterate command 638 to game 634. The iterate command causes the protagonist 664 to increase its score by one and to compare the score to threshold value 668. Since the score is now one and the threshold value is one, game 634 fires trigger 676 from its x-port 678. Trigger 676 conveys a message 680 that indicates that a pattern has been detected involving a negative hysteresis scenario which culminated with an AR event. Message 680 is conveyed specifically as "NAHYST ENTRY AR". Trigger 676 can be delivered to an algorithm (not shown) configured to utilize the detected pattern to effect patient therapy. In this instance, trigger 676 is also routed back to counter 632 to issue a start command 682. The start command makes counter 632 one again receptive to iterate, alternate and stop commands.

In the example described above, if the event following the one that caused counter 632 to reach its threshold is a PR event embodied as trigger 628, then an alternate command 642 is issued to game 634. The alternate command causes the antagonist 666 to reach its threshold 670 and fire trigger 684 from its y-port 686. Trigger 684 conveys a message 688 that indicates that a pattern has been detected involving a negative hysteresis scenario which culminated with a PR event. Message 688 is conveyed as "NAHYST ENTRY PR", Trigger 684 can be delivered to an algorithm (not shown) configured to utilize the detected pattern to effect patient therapy. In this instance, trigger 684 is routed back to counter 632 to issue a start command 690. Further, as mentioned above, data-driven pattern detection network 600 can be reconfigured to detect new and/or different patterns simply by editing the configuration data. In this example, the configuration data is embodied as the Boolean condition 614, threshold value n 646, and threshold values 668, 670.

FIG. 7 illustrates a hypothetical example of another data-driven pattern detection network 700 which utilizes the basic pattern detection objects described above in relation to FIG. 3 to detect another different pattern. This pattern detection network is configured to detect patterns involving blood chemistries, such as, for example, oxygen concentration, carbon dioxide concentration, electrolyte concentration, or enzyme concentration. Data-driven pattern detection network 700 is configured to determine a pattern where the blood chemistry value is trending outside of an allowed range either high or low. For purposes of explanation assume that the blood chemistry at issue is the electrolyte potassium ($K^+$).

A sampled value 702 for K+ is received by the pattern detection network at 700. The sampled value is subject to two guard conditions 704, 706. Guard 704 establishes whether the sampled value 702 is above a pre-established normal or tolerated range as indicated at 708. Guard 706 establishes whether the sampled value is below a pre-established normal range as indicated at 710.

Assume for purposes of example that the sampled value 702 is above the normal range. As indicated at 712 this on true condition causes guard 704 to fire trigger 714. The trigger contains a high value message 716. Alternatively, when the sampled value is below the normal range, an on true condition 718 causes guard 706 to fire trigger 720. The trigger 720 contains a low value message 722.

The sampled value 702 is also connected to two games 724, 726. Reception of the sampled value causes a start command 728 and then an alternate command 730 to be issued to games 724, 726. In an instance, where the sampled value 702 satisfies guard condition 704 (e.g., the sample is higher than the normal range) then guard 704 issues start and iterate commands 731, 732 to game 724. In an instance, where the sampled value 702 satisfies guard condition 706 (e.g., the sample is lower than the normal range) then guard 706 issues start and iterate commands 733, 734 to game 726.

Game 724 has a protagonist 735 having a threshold value set at 5 as indicated at 736 and an antagonist 737 having a threshold value set at 8 as indicated at 738. Similarly, game 726 has a protagonist 740 having a threshold value 741 set at 5 and an antagonist 742 having a threshold value set at 8 as indicated at 743. An occurrence of sampled value 702 scores a point for antagonists 737 and 742 of games 724, 726 respectively as evidenced by alternate command 730. In an instance where the sampled value 702 also satisfies guard condition 704 (e.g., is above the normal value range) then a point is also scored to protagonist 735. Conversely if the sampled value also satisfies guard condition 706 (e.g., is below the normal value range) then a point is also scored to protagonist 740 of game 726. To summarize, games 724 and 726 serve to detect whether either 5 high or 5 low sampled values 702 occur in 8 or less sampled values.

Games 724, 726 are coupled to a game 744 and a timeX 746. As will be described below, games 724, 726 function as competing players of game 744 for a period of time defined by timeX 746. Game 744 has protagonist 748 and antagonist 749 having threshold values set at 3 as indicated at 750, 751 respectively. In game 744 the protagonist 748 and antagonist 749 compete against one another and also against a time constraint defined by timeX 746 as described below.

TimeX 746 relates to a recurring condition as indicated at 754 and has a sleep time 756 set at 60 minutes as indicated at 758. If protagonist 748 of game 744 wins (e.g. gets a score 3 before the antagonist and before the timeX's time expires) then a trigger 760 indicating a high trend message 761 is sent from x-port 762. Trigger 760 delivers a restart command 764 to timeX 746. Similarly, if antagonist 749 wins (e.g., meets its threshold before the protagonist and before time expires) then a trigger 766 is sent from y-port 768 indicating a trend low message 769. Trigger 766 delivers a restart command 770 to timeX 746. Once timeX 746 is restarted, the competitors of game 744 once again have 60 minutes to meet their threshold. At the conclusion of 60 minutes without either competitor meeting its threshold and issuing a restart command 764 or 770 to timeX 746, the timeX issues a restart command 772 to game 744 which causes the protagonist and antagonist 748, 749 scores to be reset to zero and to start the game again.

In summary, games 724, 726 serve to detect high and low patterns respectively. Game 744 and timeX 746 serve to detect a trend in the patterns detected by games 724, 726. Specifically, whether three high or three low patterns are detected in less than 60 minutes. An algorithm (not shown) can receive triggers 760, 766 and effect patient treatment accordingly. As mentioned above different patterns can be detected simply by changing the configuration data. In this example the configuration data is the guard condition of guards 704, 706, the threshold values of games 724, 726 and 744 and the sleep time duration of timeX 746.

FIGS. 4 and 6-7 describe examples of data-driven objects and how one or more objects can be inter-related as a data-driven pattern detection network to detect a desired pattern. Further, these examples illustrate how configuration data of one or more data-driven objects can be changed to cause a different pattern to be detected. Data-driven pattern detection networks offer but one technique for employing competition models on an IMD to detect patterns from patient data obtained by the IMD.

Operation

FIG. 8 shows an exemplary implantable medical device (IMD) data processing technique 800 for sensing patterns in IMD data. Technique 800 may be implemented in connection with any suitably configured implantable devices and systems such as those described above. Aspects of the process may be implemented in hardware, firmware, or software, or a combination thereof. Technique 800 is shown as a set of blocks that specify operations performed by or in relation to the IMD. Blocks 802-804 represent a general technique for detecting patterns in patient data on an IMD. Blocks 806-808 and 810-814 represent examples of implementations which can facilitate accomplishing the technique described in relation to block 804.

At block 802, patient data is sensed. The patient data can be any type of patient data such as cardiac related data, blood chemistry data, and endocrine function data, among others. The patient data may be sensed by an IMD. Alternatively or additionally, some of the patient data may be sensed by a different device and gathered by the IMD through a communication mechanism for processing.

Competition models are employed to detect a pattern of the sensed patient data at block 804. Competition models track competing data events. A data event or series of data events which satisfies a set of conditions before an alternative event or series of events satisfies an alternative set of conditions can be indicative of a detected pattern.

Consistent with one technique, at block 806, an algorithm is selected for use on an implantable medical device (IMD) to effect patient therapy. The algorithm can utilize a pattern detected from sensed patient data to effect patient therapy. For instance, if hypothetical pattern x is detected then the algorithm causes hypothetical function y.

In recognition of the pattern utilized by the algorithm, configuration data is associated with a set of data-driven pattern detection objects to drive the set to detect the pattern from sensed patient data at 808. Examples of data-driven pattern detection objects are described above in relation to FIGS. 2-7. The set may, in some instances, detect one or more preliminary patterns, the detection of which can be utilized as input or commands for ultimately detecting the pattern. Examples of such techniques are employed in relations to FIGS. 4 and 6-7 above.

Configuration data can be associated with individual data-driven objects to specify the pattern to be detected. Configuration data can be changed to detect different patterns without changing individual data-driven objects and/or their inter-relationships. The configuration data specifies competitive events which can be tracked by the data-driven object. A pattern is detected when an event or events satisfies the conditions at the exclusion of the competing events.

Individual data-driven objects are selected from a set of available data-driven objects stored on an implantable medical device (IMD) at 810. For instance, specific data-driven objects may have already been tested and approved on a given IMD model. In some of these instances, the data-driven objects may already be stored on the IMDs memory. In such instances, individual data-driven objects can be selected to collectively detect the pattern.

Individual data-driven objects are communicably coupled at block 812. Communicably coupling individual data-driven objects inter-relates the data-driven objects to allow them to collectively detect a desired pattern. Examples of such inter-related data-driven objects are described above in relation to FIGS. 3-4 and 6-7.

At block 814, configuration data is associated with individual data-driven objects such that the communicably coupled individual objects can detect a desired pattern from patient data obtained by the IMD. The configuration data specifies conditions or patterns to be detected by individual data-driven objects and can be changed without altering the object. The configuration specifies competitive events which can be tracked by the data-driven object. A pattern is detected when an event or events satisfies the conditions at the exclusion of the competing events.

CONCLUSION

The foregoing discussion describes techniques for employing competition models on an IMD to detect patterns in sensed patient data. Although the inventive concepts have been described in language specific to structural features and/or methodological acts, it is to be understood that the subject matter defined in the appended claims is not necessarily limited to the specific features or acts described. Rather, the specific features and acts are disclosed as exemplary forms of implementing the claimed inventive concepts.

What is claimed is:

1. A method comprising:
selecting individual data-driven objects from a set of available data-driven objects stored on an implantable medical device (IMD), wherein the selecting comprise selecting at least a trigger, a stimulus, and a receptor;
communicably coupling individual objects; and
associating configuration data with individual objects such that the communicably coupled individual objects can detect a desired pattern from patient data obtained by the IMD.

2. The method as recited in claim 1, wherein the selecting comprises selecting data-driven objects from a set of available data-driven objects which have been previously tested on the IMD.

3. The method as recited in claim 1, wherein the communicably coupling comprises coupling individual objects into a first sub-set configured to detect a first pattern and coupling individual objects into a second sub-set configured to receive the first pattern and detect the desired pattern.

4. The method as recited in claim 1, wherein the associating comprises supplying a Boolean condition to a guard data driven object.

5. The method as recited in claim 1, further comprising in an instance where the desired pattern is detected, notifying an algorithm operable to utilize the desired pattern in effecting patient therapy.

6. The method as recited in claim 1, wherein the receptor includes at least one reactor, the method further including using the at least one reactor to compare at least two competing events in order to detect a desired pattern from patient data obtained by the IMD.

7. The method as recited in claim 6, wherein the at least one reactor comprises one or more games, the method further comprising using the one or more games to model a competition between two opponents patterns in order to detect a desired pattern from patient data obtained by the IMD.

8. The method of claim 7, wherein the one or more games comprise threshold values and the configuration data comprises the threshold values of the game.

9. The method as recited in claim 6, wherein the at least one reactor comprises one or more counters, the method further comprising using the one or more counters to count occurrences of events and/or patterns.

10. The method as recited in claim 6, wherein the at least one reactor comprises one or more timeX, the method further comprising using the timeX to compare one or more conditions against a time duration in order to detect a desired pattern from patient data obtained by the IMD.

11. The method of claim 10, wherein the one or more timeX comprises a sleep time duration and the configuration data comprises the sleep time duration of timeX.

12. The method of claim 11, wherein the game comprises threshold values, timeX comprises a sleep time duration, and the guard comprises guard conditions and wherein the configuration data comprises the threshold values of the game, the guard conditions, and the sleep time duration of timeX.

13. The method as recited in claim 6 further comprising at least one of starting, stopping, iterating and alternating the reactor in order to detect a desired pattern from patient data obtained by the IMD.

14. The method as recited in claim 6, wherein the reactor fires a trigger after a delay.

15. The method as recited in claim 1, wherein the receptor comprises at least a reactor and a guard, wherein the reactor is driven by one or more triggers and wherein the method further comprises firing one or more triggers in order to detect a desired pattern from patient data obtained by the IMD.

16. The method as recited in claim 1, further comprising receiving notification from the data-driven pattern detection network when the pattern is detected, and affecting patient therapy based at least in part on the notification.

17. The method as recited in claim 1, further comprising:
detecting a desired pattern from patient data obtained by the IMD using communicably coupled individual objects;
sending notification to timing control circuitry of the IMD when the desired pattern is detected; and
using the timing control circuitry to affect timing of one or more parameters of the IMD when the notification is received.

18. The method as recited in claim 1, wherein the receptor comprises a guard, the method further comprising using the guard to constrain delivery of stimuli to one or more receptors.

19. The method as recited in claim 1, further comprising changing the configuration data such that the communicably coupled individual objects can detect a different desired pattern from patient data obtained by the IMD.

20. The method as recited in claim 19, wherein neither the individual data-driven objects nor their coupling are changed in order to change the desired pattern.

* * * * *